US006423696B1

(12) United States Patent
Collins et al.

(10) Patent No.: US 6,423,696 B1
(45) Date of Patent: Jul. 23, 2002

(54) INHIBITION OF ARYLAMINE N-ACETYL TRANSFERASE

(75) Inventors: Jerry M. Collins, Rockville; Raymond W. Klecker, Silver Spring; Aspandiar G. Katki, Gaithersburg, all of MD (US)

(73) Assignee: The United States of America, as represented by the Department of Health & Human Services, Washington, DC (US)

( * ) Notice: Subject to any disclaimer, the term of this patent is extended or adjusted under 35 U.S.C. 154(b) by 0 days.

(21) Appl. No.: 09/549,793

(22) Filed: Apr. 14, 2000

Related U.S. Application Data

(60) Provisional application No. 60/129,687, filed on Apr. 16, 1999.

(51) Int. Cl.[7] ............................................... A61K 31/60
(52) U.S. Cl. ...................................................... 514/159
(58) Field of Search .......................................... 514/159

(56) References Cited

U.S. PATENT DOCUMENTS

| 5,527,677 A | 6/1996 | Deguchi et al. ................ 435/6 |
| 5,795,724 A | 8/1998 | Hillman .......................... 435/6 |

OTHER PUBLICATIONS

Lutoslawska, "Isoniazid metabolism in the small intestine wall of rats", Acta Pol. Pharm. (1981), 38(6), pp. 711–715, abstract.*

Cribb et al., "Expression of Monomorphic Arylamine N–Acetyltransferase (NAT1) in Human Leukocytes," *Journal of Pharmacology and Experimental Therapeutics*, vol. 259, No. 3, pp. 1241–1246 (1991).

Cribb et al., "Role of Polymorphic and Monomorphic Human Arylamine N–Acetyltransferases in Determining Sulfamethoxazole Metabolism," *Biochemical Pharmacology*, vol. 45, No. 6, pp. 1277–1282 (1993).

Frederickson et al., "Relationship between in Vivo Acetylator Phenotypes and Cytosolic N–Acetyltransferase and O–Acetyltransferase Activities in Human Uroepithelial Cells," *Cancer Epidemiology Biomarkers and Prevention*, vol. 3, No. 1, pp. 25–32 (1994).

Lang, "Acetylation as an Indicator of Risk," *Environmental Health Perspectives*, vol. 105, Supplement 4, pp. 763–766 (Jun. 1997).

Lo et al., "The Effect of Sulinadac on Arylamine N–acetyltransferase activity in *Pseudomonas aeruginosa*," *Microbios* vol. 93, pp. 159–168 (1998).

* cited by examiner

*Primary Examiner*—Kevin E. Weddington
(74) *Attorney, Agent, or Firm*—Leydig, Voit & Mayer, Ltd.

(57) ABSTRACT

The present invention is directed to a method of inhibiting arylamine N-acetyl transferase (NAT) from acetylating an arylamine group in a substrate. The method comprises contacting NAT with an inhibitor that interacts with NAT and thereby inhibits NAT from acetylating said arylamine group in said substrate. Preferably, NAT is in vivo, such as in a mammal, and the substrate is a drug. Preferably, the method inhibits acetylation of arylamine substrates which are inhaled, ingested, or absorbed through the skin, wherein acetylation of the substrate predisposes a mammal to a biological disorder or a disease. The present invention also provides a composition comprising a compound comprising an arylamine group and an inhibitor, wherein the inhibitor interacts with NAT to inhibit NAT from acetylating the arylamine group in the compound.

36 Claims, 5 Drawing Sheets

INHIBITION OF ARYLAMINE N-ACETYL TRANSFERASE

This application claims priority to U.S. provisional patent application Serial No. 60/129,687, filed Apr. 16, 1999.

TECHNICAL FIELD OF THE INVENTION

The present invention relates to the inhibition of acetylation of a substrate by arylamine N-acetyl transferase.

BACKGROUND OF THE INVENTION

The majority of drugs are metabolized by enzymes in the body. Since many patients are simultaneously treated with two or more drugs, there is always the potential that one drug may interfere with the metabolism of another drug, e.g., one may inhibit the enzyme which transforms another. Inhibition of the metabolism of one drug by another drug is normally problematic. Metabolic drug-drug interactions can produce adverse reactions and nearly always require adjustments of doses. Such situations are nuisances and are desirably avoided.

Information on drug metabolism varies from one class of enzymes to another. For some drug-metabolizing enzymes (e.g., the cytochrome P450), literature on drug—drug interactions is voluminous. In contrast, very little has been reported for the arylamine N-acetyl transferases (NAT), i.e., enzymes which acetylate arylamine groups.

Unlike the wide variety of forms for cytochrome P450 and UDP-glucuronyl transferases, there are only two forms of human arylamine N-acetyl transferase, namely, NAT-1 and NAT-2. The level of expression varies substantially among individuals for both NAT-1 and NAT-2. NAT-2 is strongly polymorphic; indeed, it was the first enzyme for which polymorphism in human drug metabolism was appreciated. Among various ethnic populations, 30–80% of individuals are "fast" acetylators via NAT-2, and the remainder are "slow" acetylators. The polymorphism of NAT-1 has only recently been appreciated.

Others have described N-acetyl transferases which do not play a role in enzyme metabolism. For example, Hillman et al. (U.S. Pat. No. 5,795,724) disclose an N-acetyl transferase (NACTH) responsible for histone acetylation. NACTH differs from NAT in biological function and location in the cell. NACTH acts upon an entirely different family of substrates than NAT. In addition, NACTH is found in the nucleus of the cell, whereas NAT is located in the cytoplasm.

A number of compounds are known in the art which have arylamine groups that can be acetylated by NAT. For example, para-amino-benzoic acid (PABA), para-amino-salicylate (PAS) and sulfamethoxazole (SMX) are acetylated by NAT-1. PABA is well-known as a topical sunscreen. PAS is used for the therapy of tuberculosis, but even with the recent increase in tuberculosis, incidence of tuberculosis is still rare, and there are other more active drugs. SMX is commonly prescribed for the treatment of infections in the urinary tract and elsewhere. Drugs identified as being acetylated by NAT-2 are numerous and include isoniazid (INH), dapsone (DDS), sulphamethazine (SMZ), aminoglutethimide (AG), procainamide, and hydralazine.

Occasionally, situations arise in which it is desirable to inhibit the activity of a drug-metabolizing enzyme. Such situations include stretching a scarce or expensive supply of drugs (e.g., cyclosporin/ketoconazole), prolonging the half-life of an active drug to reduce the frequency of administration (e.g., AZT/probenecid), and blocking formation of a toxic metabolite (e.g., in cases of methanol poisoning, the use of ethanol to prevent formation of formaldehyde as a metabolite of methanol).

Oftentimes for NAT, it is desirable to inhibit the formation of a toxic metabolite. In some cases, the acetylated metabolite generated by NAT has been shown definitively to be more toxic than the parent drug. In other cases, there is not a direct link to a specific metabolite, but there is a strong association between high rates of acetylation and adverse reactions. As an extension of this category, even in the absence of drug therapy, there have been several linkages reported between acetylation rates and predisposition to diseases such as cancer. In certain situations, individuals with rapid acetylation have a 10-fold (or greater) risk of disease than individuals with slow acetylation (Lang et al. *Environmental Health Perspectives* 105(suppl. 4): 763–766 (1997)). For these situations, inhibition of NAT would be beneficial to patients.

Therefore, there exists a need for a method of inhibiting the acetylation of a substrate by NAT. The present invention seeks to provide such a method, as well as a composition for use in such a method. These and other objects and advantages of the present invention, as well as additional inventive features, will be apparent from the description of the invention provided herein.

BRIEF SUMMARY OF THE INVENTION

The present invention is directed to a method of inhibiting arylamine N-acetyl transferase (NAT) from acetylating an arylamine group in a substrate. The method comprises contacting NAT with an inhibitor that interacts with NAT and thereby inhibits NAT from acetylating the arylamine group in the substrate. Preferably, the inhibitor of NAT is a compound of formula:

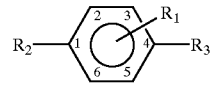

wherein one or more carbon atoms at positions 2, 3, 5 and 6 can be heteroatoms, which can be the same or different and can be selected from the group consisting of oxygen, nitrogen and sulfur, $R_1$ is one or more substituents, which can be the same or different, selected from the group consisting of hydrogen, hydroxy, an alkoxy, sulfhydryl, nitro, amino, a halo, an aryloxy, cyano, —[$SO_2$—$R_4$], an alkyl, a cycloalkyl, a heterocycloalkyl, an alkenyl, an alkynyl, an aryl, a heteroaryl, an arylalkyl and a heteroarylalkyl, $R_2$ is a substituent selected from the group consisting of amino, carboxyamide, sulfamide, —[NH—$NH_2$], —[$SO_2$—NH—$NH_2$] and —[CO—NH—$NH_2$], and $R_3$ is a substituent selected from the group consisting of hydrogen, hydroxy, an alkoxy, sulfhydryl, nitro, amino, a halo, an aryloxy, cyano, —[$SO_2$—$R_4$], an alkyl, a cycloalkyl, a heterocycloalkyl, an alkenyl, an alkynyl, an aryl, a heteroaryl, an arylalkyl, a heteroarylalkyl, wherein $R_4$ is a substituent selected from the group consisting of hydrogen, hydroxy, an alkoxy, sulfhydryl, nitro, amino, a halo, an aryloxy, cyano, an alkyl, a cycloalkyl, a heterocycloalkyl, an alkenyl, an alkynyl, an aryl, a heteroaryl, an arylalkyl, a heteroarylalkyl, and NH—$R_5$, wherein $R_5$ is a substituent selected from the group consisting of hydrogen, hydroxy, an alkoxy, sulfhydryl, nitro, amino, a halo, an aryloxy, cyano, an alkyl, a cycloalkyl, a heterocycloalkyl, an alkenyl, an alkynyl, an aryl, a heteroaryl, an arylalkyl and a heteroarylalkyl, wherein the substituent is unsubstituted or substituted with one to three groups, which may be the same or different and are selected from the group consisting of an alkyl, an alkenyl, an alkynyl, =O, a halo, hydroxy, a lower alkoxy, carboxy, a carboalkoxy, a carboxamido, cyano, carbonyl, —NO$_2$, an alkylthio, sulfoxide, sulfone, acylamino, amidino, an aryl, a heteroaryl, an aryloxy, and a heteroaryloxy.

The present invention also provides a composition comprising a compound comprising an arylamine group that can be acetylated by NAT and an inhibitor which interacts with NAT to inhibit NAT from acetylating the arylamine group in the compound.

The invention may best be understood with reference to the accompanying drawings and in the following detailed description of the preferred embodiments.

DESCRIPTION OF THE PREFERRED EMBODIMENTS

Figure 1:
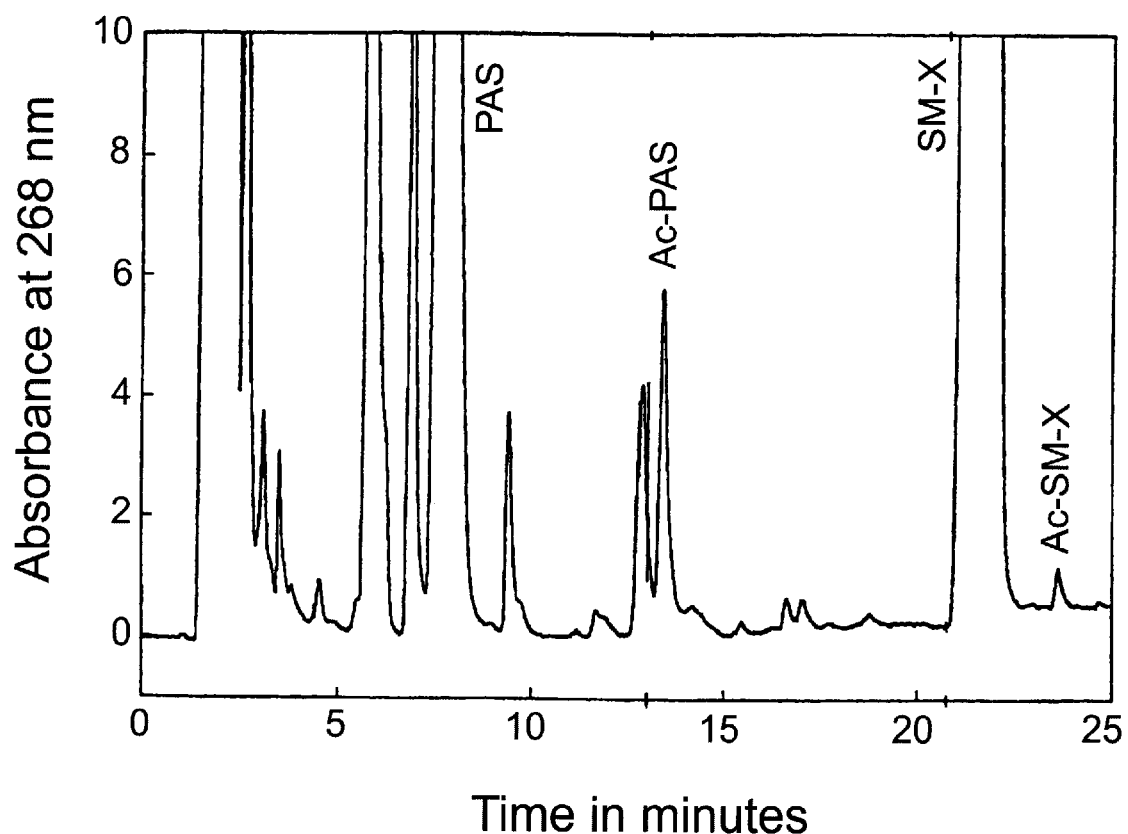
FIG. 1 is a graph of absorbance at 268 nm vs. time (minutes).

The present invention provides a method of inhibiting arylamine N-acetyl transferase (NAT) from acetylating an arylamine group in a substrate. The method comprises contacting NAT with an inhibitor that interacts with NAT and thereby inhibits NAT from acetylating the arylamine group in the substrate. Preferably, NAT is in vivo. More preferably, NAT is in a mammal, most preferably a human.

Any inhibitor of NAT can be used in the methods of the present invention as long as it is safe and efficacious. By "inhibitor" is meant any agent that inhibits NAT from acetylating an arylamine group in a substrate. While desirably an inhibitor effects complete inhibition, one of ordinary skill in the art will appreciate that less than complete inhibition is beneficial in the context of the present inventive method. In this regard, an inhibitor can inhibit NAT by binding NAT in such a place and in such a manner as to affect adversely NAT's ability to acetylate a substrate. For example, an inhibitor can bind NAT at or near the active site of the enzyme such that NAT is unable to bind to or acetylate a substrate. One of ordinary skill in the art will appreciate that binding of an inhibitor at the active site will interfere with the ability of NAT to bind a substrate and that binding of an inhibitor near the active site can effect a conformational change at or near the active site such that NAT cannot bind or acetylate a substrate. Examples of such inhibitors include immunological reagents, such as antibodies, e.g., monoclonal and polyclonal antibodies and immunologically reactive fragments thereof. The generation of immunological reagents is within the skill in the art. Alternatively, the inhibitor is, itself, a substrate of NAT, in which case the inhibitor comprises an arylamine group that can be acetylated by NAT. As such, the inhibitor functions as a competitive inhibitor of the substrate. Suitable inhibitors can be determined in accordance with the assays set forth in Examples 1 and 2. In addition, wherein the inhibitor is a substrate of NAT, it is preferred that acetylation of the inhibitor does not result in a toxic or carcinogenic product. Preferably, the inhibitor of NAT is a compound of formula:

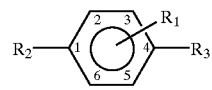

wherein one or more carbon atoms at positions 2, 3, 5 and 6 can be heteroatoms, which can be the same or different and can be selected from the group consisting of oxygen, nitrogen and sulfur, $R_1$ is one or more substituents, which can be the same or different, selected from the group consisting of hydrogen, hydroxy, an alkoxy, sulfhydryl, nitro, amino, a halo, an aryloxy, cyano, —[SO$_2$—R$_4$], an alkyl, a cycloalkyl, a heterocycloalkyl, an alkenyl, an alkynyl, an aryl, a heteroaryl, an arylalkyl, and a heteroarylalkyl, $R_2$ is a substituent selected from the group consisting of amino, carboxyamide, sulfamide, —[NH—NH$_2$], —[SO$_2$—NH—NH$_2$] and —[CO—NH—NH$_2$], and $R_3$ is a substituent selected from the group consisting of hydrogen, hydroxy, an alkoxy, sulfhydryl, nitro, amino, a halo, an aryloxy, cyano, —[SO$_2$—R$_4$], an alkyl, a cycloalkyl, a heterocycloalkyl, an alkenyl, an alkynyl, an aryl, a heteroaryl, an arylalkyl and a heteroarylalkyl, wherein $R_4$ is a substituent selected from the group consisting of hydrogen, hydroxy, an alkoxy, sulfhydryl, nitro, amino, a halo, an aryloxy, cyano, an alkyl, a cycloalkyl, a heterocycloalkyl, an alkenyl, an alkynyl, an aryl, a heteroaryl, an arylalkyl, a heteroarylalkyl, and NH—R$_5$, wherein R$_5$ is a substituent selected from the group consisting of hydrogen, hydroxy, an alkoxy, sulfhydryl, nitro, amino, a halo, an aryloxy, cyano, an alkyl, a cycloalkyl, a heterocycloalkyl, an alkenyl, an alkynyl, an aryl, a heteroaryl, an arylalkyl and a heteroarylalkyl, wherein the substituent is unsubstituted or substituted with one to three groups, which can be the same or different and can be selected from the group consisting of an alkyl, an alkenyl, an alkynyl, =O, a halo, hydroxy, a lower alkoxy, carboxy, a carboalkoxy, a carboxamido, cyano, carbonyl, —NO$_2$, an alkylthio, sulfoxide, sulfone, acylamino, amidino, an aryl, such as phenyl and benzyl, a heteroaryl, an aryloxy, such as phenoxy and benzyloxy, and a heteroaryloxy.

"Alkyl" includes linear and branched alkyl groups, such as alkyl groups of twenty carbons or less, preferably from about 1 to about 10 carbon atoms, more preferably from about 1 to about 8 carbon atoms, and most preferably from about 1 to about 6 carbon atoms. Examples of such alkyl radicals include methyl, ethyl, propyl, isopropyl, n-butyl, isobutyl, tert-butyl, pentyl, isoamyl, hexyl, octyl, dodecanyl, and the like. "Cycloalkyl" includes cyclic alkyl groups, which comprise a linear and/or branched alkyl group, preferably twenty carbons or less. Preferably, the cycloalkyl comprises a cyclic $C_3$-$C_8$ alkyl group.

"Heterocycloalkyl" includes a cyclic alkyl group as described above in which at least one of the methylene groups is replaced by a heteroatom, such as a nitrogen or sulfur, which may be unsubstituted or substituted. Examples of heterocycloalkyls include tetrahydrofuranyl, piperidine and the like.

"Alkenyl" includes a hydrocarbon of a linear, branched or cyclic configuration and combinations thereof, which comprises at least one double bond. Preferably, the alkenyl comprises from about 2 to about 20 carbon atoms, preferably from about 2 to about 10 carbon atoms, more preferably from about 2 to about 8 carbon atoms, and most preferably from about 2 to about 6 carbon atoms. Examples of alkenyl radicals include vinyl, allyl, 1,4-butadienyl, isopropenyl, and the like.

"Alkynyl" includes a hydrocarbon of a linear or branched configuration and combinations thereof, which comprises at least one triple bond and comprises from about 2 to about 20 carbon atoms, preferably from about 2 to about 10 carbon atoms, more preferably from about 2 to about 8 carbon atoms, and most preferably from about 2 to about 6 carbon atoms. Examples of alkynyl radicals include ethynyl, propynyl (propargyl), butynyl, and the like.

"Aryl" and "heteroaryl" include a 5- or 6-membered aromatic or heteroaromatic ring containing one or more heteroatoms, preferably no more than three heteroatoms, which are selected from the group consisting of oxygen, nitrogen and sulfur, a bicyclic 9- or 10-membered aromatic or heteroaromatic ring system containing one or more heteroatoms, preferably no more than three heteroatoms, which are selected from the group consisting of oxygen, nitrogen and sulfur. Examples of aryl groups include, for example, phenyl, naphthyl, and biphenyl groups. Examples of heteroaryls include, for example, imidazole, thiophene, and oxazole groups. The aryl and heteroaryl groups can be substituted with one or more groups, preferably no more than three groups, selected from the group consisting of an unsubstituted or a substituted $C_1$–$C_8$ alkyl, an alkenyl, an alkynyl, $=O$, —$NO_2$, halo, hydroxy, alkoxy, carboxy, a carboalkoxy, a carboxamido, —$OCH(COOH)_2$, cyano, a carbonyl, an alkylthio, sulfoxide, sulfone, an acylamino, amidino, an aryl, such as phenyl or benzyl, an aryloxy, such as phenoxy or benzyloxy, heteroaryl and heteroaryloxy, wherein each of said aryl, aryloxy, heteroaryl and heteroaryloxy is optionally substituted with one or more groups, preferably no more than three groups, which are selected from the group consisting of a $C_1$–$C_8$ alkyl, an alkenyl, an alkynyl, $=O$, a halo, a hydroxyl, an alkoxy, carboxy, a carboalkoxy, a carboxamido, cyano, carbonyl, an alkylthio, sulfoxide, sulfone, an acylamino, amidino, an aryl, such as phenyl or benzyl, an aryloxy, such as benzyloxy, carboxamido, a heteroaryl, a heteroaryloxy and —$NO_2$. By "arylalkyl" and "heteroarylalkyl" is meant an aryl or heteroaryl group additionally comprising a linear or branched alkyl group, preferably of twenty carbons or less.

The term "alkoxy" as used herein means an alkyl group as defined herein, wherein at least one alkyl hydrogen atom is replaced by an oxygen atom. Examples of alkoxy groups include, for example, methoxy, ethoxy, isopropoxy, and the like. By "aryloxy" and "heteroaryloxy" is meant an aryl or a heteroaryl group as defined herein, wherein at least one aryl or heteroaryl hydrogen atom is replaced by an oxygen atom.

"Halo" can be any suitable halogen. Preferably, "halo" is fluorine, chlorine, bromine or iodine.

Alkyl, cycloalkyl, heterocycloalkyl, alkenyl and alkynyl can be unsubstituted or substituted with one or more groups, preferably no more than three groups, which are selected from the group consisting of an alkyl, an alkenyl, an alkynyl, $=O$, a halo, hydroxy, a lower alkoxy, preferably of twenty carbons or less, carboxy, a carboalkoxy, a carboxamido, cyano, carbonyl, —$NO_2$, an alkylthio, sulfoxide, sulfone, acylamino, amidino, an aryl, such as phenyl or benzyl, a heteroaryl, an aryloxy, such as phenoxy or benzyloxy, and a heteroaryloxy, wherein aryl, heteroaryl, aryloxy and heteroaryloxy can be substituted as well.

As stated above, there are only 2 forms of human arylamine N-acetyl transferase, namely, NAT-1 and NAT-2. The inhibitor for use in the inventive method can be an inhibitor of either NAT-1 or NAT-2 or both. When the inhibitor inhibits acetylation of a substrate by NAT-1, preferably the inhibitor is selected from the group consisting of para-amino-salicylate (PAS) and para-amino-benzoic acid (PABA). When the inhibitor inhibits the activity of NAT-2, the inhibitor is preferably selected from the group consisting of dichlorphenamide, sulphamethazine (SMZ), dapsone (DDS) and isoniazid (INH).

Compounds of the above formula are widely available commercially. Those compounds that are not commercially available can be readily prepared using organic synthesis methods known in the art.

A "substrate" can be any compound comprising an arylamine group which can be acetylated by NAT and includes substrates that occur naturally in the body, are ingested, whether in solid or liquid form as food or supplements, are inhaled, are absorbed through the skin, or are administered as therapeutic or prophylactic active agents, e.g., pharmaceutical agents or drugs. Such substrates are well-known in the art. Examples of suitable substrates include aminosalicylates, such as 5-aminosalicylate and its prodrug, sulfasalazine. All sulfonamides are appropriate substrates with the exception of topical creams such as sulfadoxine, sulfisoxole, sulfapyridine and sulfaphenazole. Several anti-cancer drugs are also acted upon by NAT, such as aminoglutethimide and the investigational drugs amonafide and batracylin. Substrates of NAT also include compounds found in the environment, such as substances in drinking water or tobacco smoke. Such compounds naturally comprise an arylamine group that can be acetylated by NAT or comprise an arylamine group that can be acetylated by NAT as a result of a metabolic process, e.g., an arylamine group that becomes exposed or is added as a result of a metabolic process. Substrates of NAT can be determined using the methods set forth in Example 1, for example, or other suitable methods as are known in the art.

Oftentimes, acetylation of a drug in vivo adversely affects its therapeutic or prophylactic benefit. Inhibition of acetylation of a drug by NAT can increase the drug's therapeutic effect. For example, inhibiting acetylation of a drug can increase its effective concentration or prolong its half-life in vivo.

Although metabolism generally lowers the toxicity of drugs, the opposite effect is often encountered with NAT, i.e., the metabolite is more toxic than the parent drug. The present inventive method is, therefore, also useful for reducing the formation of toxic or carcinogenic metabolites of a drug that is acetylated by NAT. If an inhibitor is co-administered with a drug in accordance with the present inventive method, toxicity to the recipient can be decreased because there will be less exposure to the toxic or carcinogenic metabolite, and the beneficial effects of the parent drug can be maximized. The present inventive method can be applied in many therapeutic areas, since drugs which are metabolized by NAT are used in most medical disciplines, including heart disease, infectious diseases, oncology and the like. In the context of the present inventive methods, "co-administered" is intended to encompass simultaneous administration of a substrate and an inhibitor as well as administration in either order and sufficiently close in time as to realize inhibition of acetylation of the substrate by NAT.

Heretofore, no one has combined a NAT inhibitor with a compound comprising an arylamine group that can be acetylated by NAT, such as a drug, in a single composition, such as a pharmaceutical composition, in order to enhance the therapeutic effect of the drug as described above.

Accordingly, the present invention also provides a composition comprising a compound comprising an arylamine group that can be acetylated by NAT, such as the substrates described above, and an inhibitor as described above. The inhibitor interacts with NAT to inhibit NAT from acetylating the arylamine group in the compound.

For example, a composition can be a water supply comprising a NAT inhibitor. The inhibitor can block acetylation of compounds known to be procarcinogenic in contaminated drinking water.

In addition to improving the therapeutic use of a variety of marketed or investigational drugs, the present inventive method can be used in the prophylaxis of biological disorders or disease in which acetylation predisposes an animal to such a biological disorder or disease. For example, many epidemiological studies have noted that a high capacity of acetylation by NAT is linked to a greater incidence of human tumors. As such, the products of acetylation are carcinogenic. According to the claimed method, an inhibitor of NAT can be administered prophylactically to reduce acetylation of a substrate, which, in turn, can lead to a decrease in a biological disorder in which NAT plays an adverse role, e.g., human cancer. One of ordinary skill in the art will appreciate that, although complete blockage of acetylation is preferred, any reduction in acetylation will be useful in the prophylaxis of a biological disorder or disease. Similarly, procarcinogens found in the environment can be ingested, absorbed through the skin, or inhaled, i.e., in tobacco smoke. The present invention is useful in inhibiting the acetylation of such compounds found in the environment, thereby attenuating the formation of carcinogenic substances in the body.

In addition to the above-described embodiments, in vitro embodiments of the present inventive methods also have utility. The present inventive method of inhibiting acetylation of a substrate by NAT can be employed for research in numerous disciplines, including enzymology and clinical pharmacology.

The skilled artisan will appreciate that suitable methods of administering an inhibitor of NAT, alone or in further combination with a substrate, e.g., the compositions described herein, are available. Although more than one route can be used to administer a particular NAT inhibitor, a particular route can provide a more immediate and more effective reaction than another route. Accordingly, the described routes of administration are merely exemplary and are in no way limiting.

The dose administered to a mammal, particularly a human, in accordance with the present invention should be sufficient to effect the desired response in the animal over a reasonable time frame. One skilled in the art will recognize that dosage will depend upon a variety of factors, including the strength of the particular substrate and NAT inhibitor employed, as well as the age, species and body weight of the animal. The size of the dose also will be determined by the route, timing and frequency of administration as well as the existence, nature, and extent of any adverse side effects that might accompany the administration of a particular substrate and NAT inhibitor and the desired physiological effect.

Suitable doses and dosage regimens can be determined by conventional range-finding techniques known to those of ordinary skill in the art. Dosages for some inhibitors suitable for use in the present invention are known to those of skill in the art as they are widely administered to patients for indications other than inhibition of acetylation of a substrate.

One of ordinary skill in the art will appreciate that the form the composition comprising a compound comprising an arylamine and a NAT inhibitor will take is determined by the particular compound (e.g., drug) and particular inhibitor (e.g., inhibitor comprising an arylamine group) used. Determination of appropriate combinations of compound and inhibitor is well within the skill in the art and, furthermore, can be determined using the methods set forth in Examples 1–3. Preferably, acetylation of the inhibitor does not result in a toxic or carcinogenic product.

Compositions for use in the present inventive method preferably comprise a carrier, such as a pharmaceutically acceptable carrier, and an amount of a NAT inhibitor sufficient to inhibit acetylation of a substrate. The carrier can be any of those conventionally used and is limited only by chemico-physical considerations, such as solubility and lack of reactivity with the compound, and by the route of administration. It will be appreciated by one of ordinary skill in the art that, in addition to the following described pharmaceutical compositions, the NAT inhibitor can be formulated as polymeric compositions, inclusion complexes, such as cyclodextrin inclusion complexes, liposomes, microspheres, microcapsules and the like.

The pharmaceutically acceptable excipients described herein, for example, vehicles, adjuvants, carriers or diluents, are well-known to those who are skilled in the art and are readily available to the public. It is preferred that the pharmaceutically acceptable carrier be one which is chemically inert to the NAT inhibitor and one which has no detrimental side effects or toxicity under the conditions of use.

The choice of excipient will be determined in part by the particular NAT inhibitor, as well as by the particular method used to administer the composition. Accordingly, there is a wide variety of suitable formulations of the pharmaceutical composition of the present invention. The following formulations are merely exemplary and are in no way limiting.

Injectable formulations are among those that are preferred in accordance with the present inventive method. The requirements for effective pharmaceutical carriers for injectable compositions are well-known to those of ordinary skill in the art (see *Pharmaceutics and Pharmacy Practice*, J. B. Lippincott Co., Philadelphia, Pa., Banker and Chalmers, eds., pages 238–250 (1982), and *ASHP Handbook on Injectable Drugs*, Toissel, $4^{th}$ ed., pages 622–630 (1986)). It is preferred that such injectable compositions be administered intramuscularly, subcutaneously, intravenously, or intraperitoneally.

Topical formulations are well-known to those of skill in the art. Formulations suitable for topical administration may be presented as creams, gels, pastes, or foams, containing, in addition to the active ingredient, such carriers as are known in the art to be appropriate. Such formulations are suitable in the context of the present invention for application to the skin.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Aerosol formulations to be administered via inhalation are also appropriate. These aerosol formulations can be placed into pressurized acceptable propellants, such as dichlorodifluoromethane, propane, nitrogen, and the like. They also can be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inhibitor can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride, with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Suitable soaps for use in parenteral formulations include fatty alkali metals, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-p-aminopropionates, and 2-alkyl-imidazoline quaternary ammonium salts, and (e) mixtures thereof.

The parenteral formulations may contain preservatives and buffers. In order to minimize or eliminate irritation at the site of injection, such compositions may contain one or more nonionic surfactants having a hydrophile-lipophile balance (HLB) of from about 12 to about 17.

The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The inhibitor of NAT and a substrate, preferably a drug, can be co-administered to inhibit acetylation of the substrate. The present inventive method also can involve the co-administration of other pharmaceutically active compounds. By "co-administration" is meant administration before, concurrently with, e.g., in combination with the NAT inhibitor in the same formulation or in separate formulations, or after administration of a NAT inhibitor as described above. For example, vitamins and minerals, e.g., zinc, anti-oxidants, e.g., carotenoids (such as a xanthophyll carotenoid like zeaxanthin or lutein), and micronutrients can be co-administered. One of ordinary skill in the art will appreciate that administration of vitamins and minerals will be particularly useful in situations wherein the present inventive method is employed as a prophylactic measure.

EXAMPLES

The following examples further illustrate the present invention but, of course, should not be construed as in any way limiting its scope.

Example 1

This example demonstrates that PAS and PABA are effective inhibitors of acetylation by NAT-1.

Subcellular Preparations

Human liver was homogenized and prepared by high-speed differential centrifugation. A preliminary centrifugation was performed at 13,000 g for 20 min. The cytosolic fraction was collected as the supernatant from a second centrifugation at 105,000 g for 60 min (105S). Upon the addition of the single cofactor for NAT, acetyl co-enzyme A, and its regenerating system, 1 mM acetyl-L-carnitine and 1 unit/ml of carnitine-acetyl transferase, the reaction proceeded following addition of the substrate, i.e., PAS, PABA or SMX, to the cytosol. Fifteen minutes at 37° C. was sufficient to generate measurable metabolites. The reaction was terminated by the addition of perchloric acid to a final concentration of 1.5%. Parallel incubations were conducted for drug alone versus drug plus potential inhibitor. Percent inhibition was calculated from the ratio of [Acetylated metabolite]/[parent] with and without the potential inhibitor.

The formation of N-acetylated metabolites was quantified by HPLC. Samples from the incubates were injected onto a reverse-phase column (e.g., Waters Symmetry C18, 5 micron, 4.6×150 mm). The mobile phase consisted of 1% acetic acid, with a gradient in acetonitrile from 7% to 19% over 16 minutes, then 19% to 37% over 10 minutes at 1 ml/min. Drugs and their N-acetylated metabolites were quantitated by UV absorption using a diode-array detector.

PAS incubation with human liver subcellular preparations as described above resulted in a single metabolic peak. Based upon retention time and UV spectrum, the peak was identified as Ac-PAS, an acetylated metabolite. Similar results were obtained for SMX as illustrated by FIG. 1, which is a graph of absorbance at 268 nm vs. time (min). FIG. 1 shows the HPLC results for PAS and SMX, along with their acetylated metabolites, Ac-PAS and Ac-SMX.

The substrates assayed above were then co-incubated with human liver subcellular preparations. Co-incubation of 200

μM of PAS with either 20 μM of PABA or 200 μM SMX resulted in blockage of all measurable acetylation to Ac-PABA and 50% inhibition of acetylation to Ac-SMX. Similarly, when 200 μM of PABA was co-incubated with either 20 μM of PAS or 200 μM of SMX, no Ac-PAS was detected and Ac-SMX formation was inhibited by 50%.

Hepatocyte Culture

Human hepatocytes were incubated at 37° C. at a ratio of 1 million cells per ml in modified Williams E buffer. Either cryopreserved hepatocytes in suspension or freshly-isolated hepatocytes attached to microtiter plates were used. The reaction was initiated by addition of substrate, and terminated after 4 hours by the addition of perchloric acid. As before, parallel incubations were conducted for drug alone versus drug plus potential inhibitors. Percent inhibition was calculated from the ratio of [Acetylated metabolite]/[parent] with and without the potential inhibitor.

Incubation of 200 μM of PAS or 200 μM of SMX separately with hepatocytes resulted in formation of Ac-PAS and Ac-SMX. When co-incubated, the same amount of Ac-PAS was found, but Ac-SMX was reduced by 60%.

The preceding results demonstrate that both PAS and PABA are effective competitive inhibitors of the acetylation of SMX by NAT-1.

Example 2

This example demonstrates that dichlorphenamide, sulphamethazine (SMZ), dapsone (DDS) and isoniazid (INH) are effective inhibitors of acetylation by NAT-2.

Subcellular Preparations

INH, DDS, SMZ were incubated with human liver subcellular preparations as described in Example 1. The reactions were allowed to proceed for thirty minutes at 37° C. before termination by addition of perchloric acid. Parallel incubations were conducted for drug alone versus drug plus potential inhibitors, namely dichlorphenamide, SMZ, INH and aminoglutethimide (AG). The formation of N-acetylated metabolites was quantified by HPLC. For INH, 1-octanesulfonic acid (5 mM) was added to the mobile phase.

Acetylated metabolites were found when INH, DDS or SMZ were incubated separately with cytosol. The cross inhibition with each other and by dichlorphenamide are shown in Table I.

TABLE I

| | Inhibitors | | | |
| Substrate | dichlorphenamide | SMZ | INH | AG |
| --- | --- | --- | --- | --- |
| DDS | ++ | ++ | ++ | (N/A) |
| SMZ | ++ | | (N/A) | ++ |
| INH | -- | (N/A) | | (N/A) |

++ = strong inhibition
-- = no inhibition
(N/A) = not tested

Hepatocyte Culture

INH, DDS and SMZ were incubated with human hepatocytes as described in Example 1. Parallel cultures were conducted for each drug alone and each drug plus dichlorphenamide as a potential inhibitor. An additional culture of DDS was incubated with SMZ, a potential inhibitor. Dichlorphenamide strongly inhibited the acetylation of all substrates. In addition, SMZ inhibited acetylation of DDS.

The preceding results illustrate that dichlorphenamide, SMZ, DDS, and INH are effective inhibitors of NAT-2.

Example 3

This example demonstrates that PAS inhibits the acetylation of SMX, when PAS and SMX are administered in vivo at their standard doses.

Based upon the in vitro results reported in Examples 1 and 2, clinical inhibition studies of acetylation were designed. SMX was given to a volunteer human subject at its standard dose of 500 mg every 12 hours, for a total of 5 days. On the fourth and fifth days, PAS was also administered at its standard dose of 4 g every 8 hours. Plasma and urine concentrations of SMX and its acetylated metabolite, Ac-SMX, were measured on the third and fifth day of dosing. Day 3 represents baseline pharmacokinetics of SMX and Ac-SMX, while Day 5 demonstrates the impact of PAS upon blocking the formation of Ac-SMX.

Figure 2:
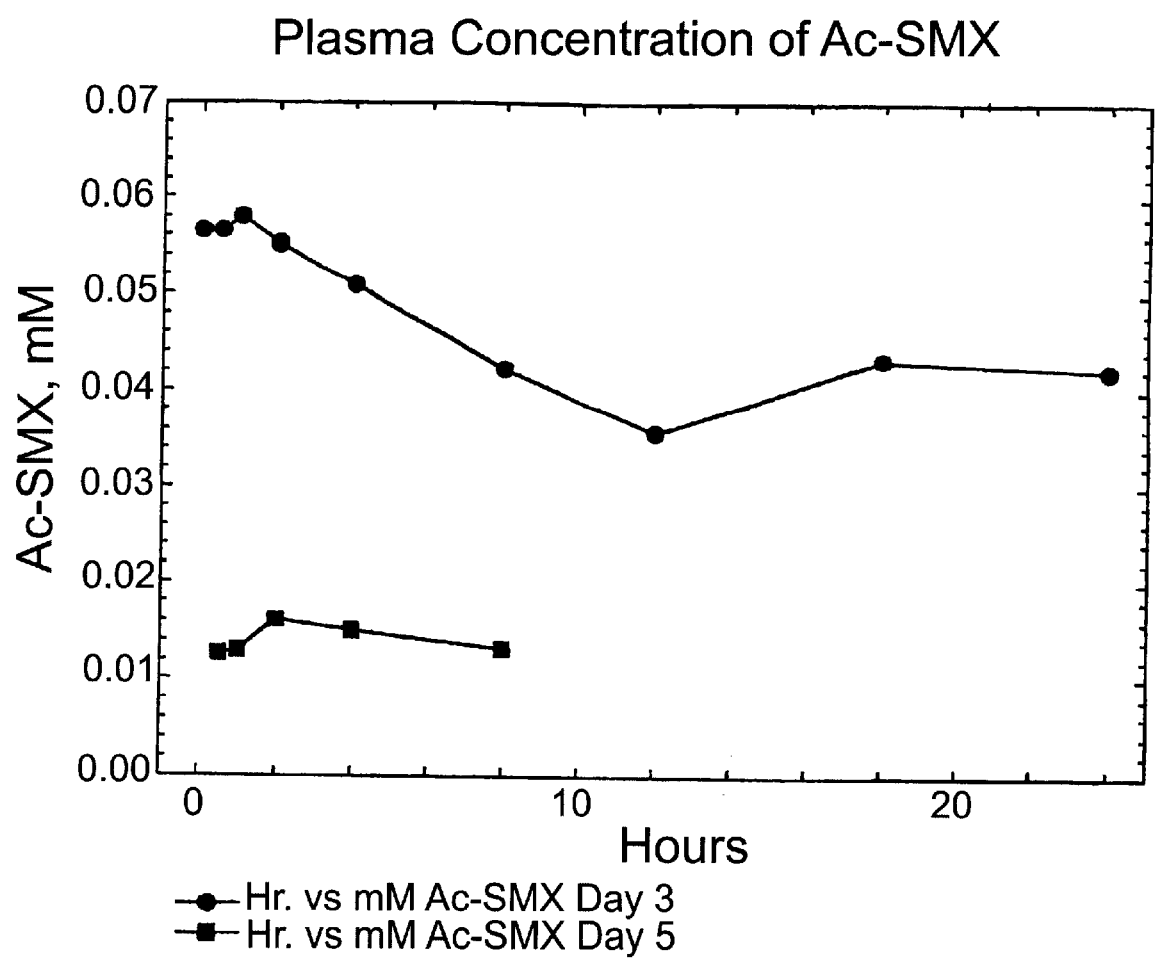
FIG. 2 is a graph of plasma concentration of Ac-SMX (mM) vs. time (hours).
Figure 3:
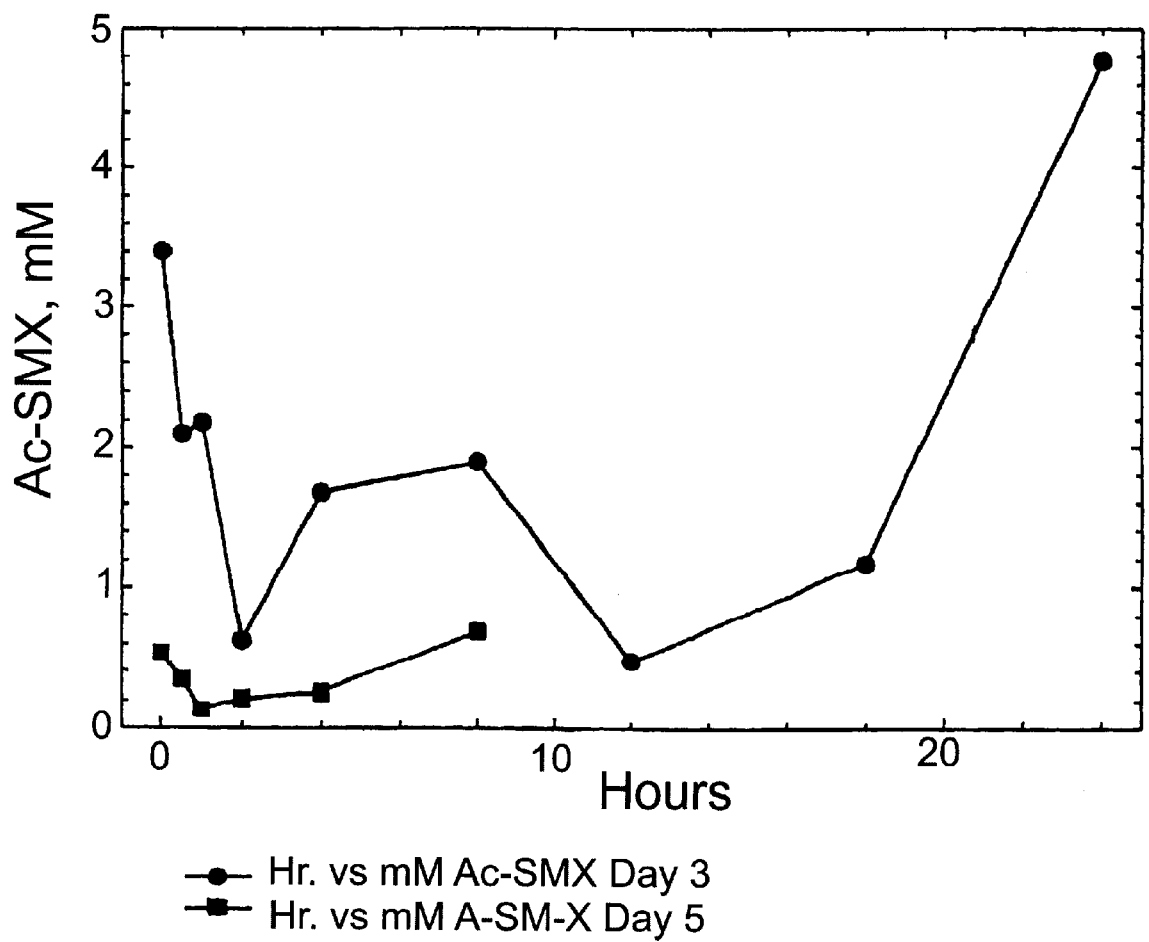
FIG. 3 is a graph of urine concentration of Ac-SMX (mM) vs. time (hours).

As shown in FIG. 2, which is a graph of the plasma concentration of Ac-SMX (mM) vs. time (hours), shows that substantial concentrations of Ac-SMX were observed in plasma on Day 3, but were almost completely abolished on Day 5, indicating essentially complete inhibition of metabolism of SMX to form Ac-SMX. In addition, substantial amounts of Ac-SMX were excreted into urine on Day 3, but not on Day 5, further reflecting successful inhibition by PAS of SMX acetylation, as illustrated in FIG. 3, which is a graph of urine concentration of Ac-SMX (mM) vs. time (hours).

Figure 4:
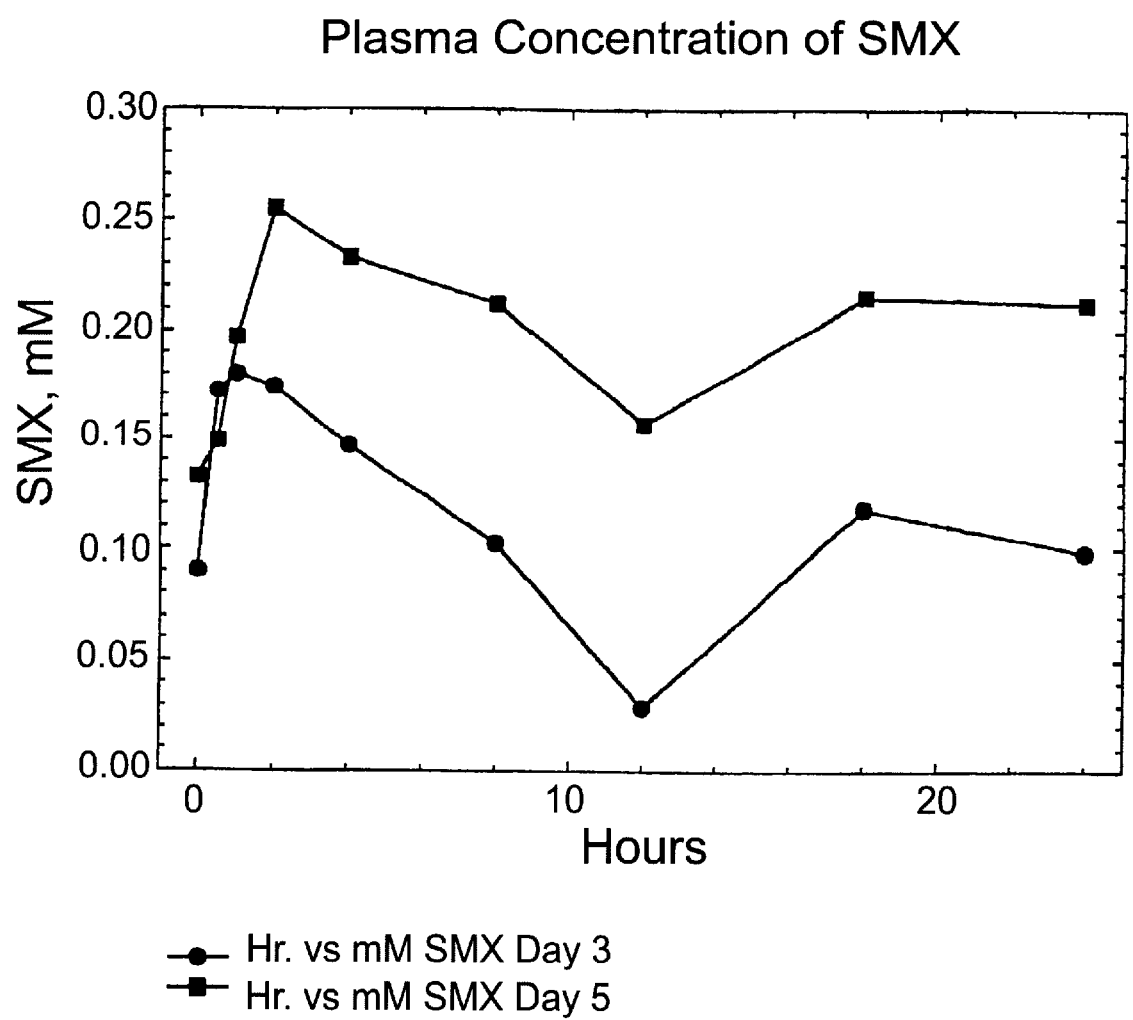
FIG. 4 is a graph of plasma concentration of SMX (mM) vs. time (hours).

Since acetylation is one of the major pathways for SMX elimination, blockage of that pathway produced higher plasma concentrations of SMX on Day 5 than on Day 3, as exemplified by FIG. 4, which is a graph of plasma concentration of SMX (mM) vs. time (hours).

Figure 5:
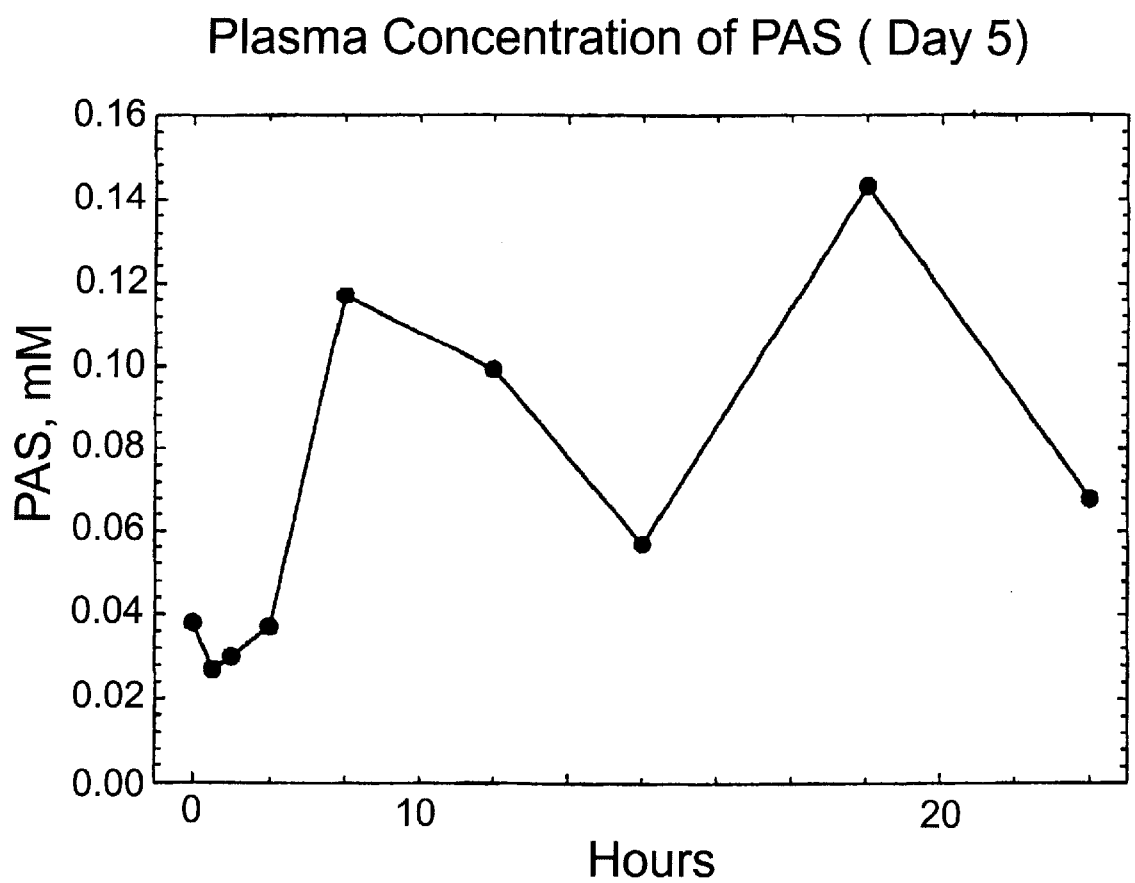
FIG. 5 is a graph of plasma concentration of PAS (mM) vs. time (hours).

At the conventional doses used in this study, the PAS concentrations in plasma, which were measured on Day 5 using HPLC as shown in FIG. 5, which is a graph of plasma concentration of PAS (mm) vs. time (hours), were found to exceed the levels required to inhibit NAT-1 in the screening experiments with human liver tissue.

This example exemplifies the ability of an inhibitor of NAT to block metabolism of a drug in vivo.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of inhibiting arylamine N-acetyl transferase (NAT) from acetylating an arylamine group in a substrate in vivo, which method comprises contacting NAT with an inhibitor that interacts with NAT in vivo and thereby inhibits NAT from acetylating said arylamine group in said substrate.

2. The method of claim 1, wherein NAT is in a mammal.

3. The method of claim 1, wherein said inhibitor comprises an arylamine group that can be acetylated by NAT.

4. The method of claim 1, wherein said inhibitor is a compound of formula:

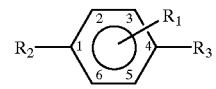

wherein one or more carbon atoms at positions 2, 3, 5 and 6 can be heteroatoms, which can be the same or different, wherein $R_1$ is one or more substituents, which can be the same or different, selected from the group consisting of hydrogen, hydroxy, an alkoxy, sulfhydryl, nitro, amino, a halo, an aryloxy, cyano, —[SO₂—R₄], an alkyl, a cycloalkyl, a heterocycloalkyl, an alkenyl, an alkynyl, an aryl, a heteroaryl, an arylalkyl and a heteroarylalkyl, wherein R₂ is a substituent selected from the group consisting of amino, carboxyamide, sulfamide, —[NH—NH₂], —[SO₂—NH—NH₂] and —[CO—NH—NH₂], wherein R₃ is a substituent selected from the group consisting of hydrogen, hydroxy, an alkoxy, sulfhydryl, nitro, amino, a halo, an aryloxy, cyano, —[SO₂—R₄], an alkyl, a cycloalkyl, a heterocycloalkyl, an alkenyl, an alkynyl, an aryl, a heteroaryl, an arylalkyl and a heteroarylalkyl, wherein R₄ is a substituent selected from the group consisting of hydrogen, hydroxy, an alkoxy, sulfhydryl, nitro, amino, a halo, an aryloxy, cyano, an alkyl, a cycloalkyl, a heterocycloalkyl, an alkenyl, an alkynyl, an aryl, a heteroaryl, an arylalkyl, a heteroarylalkyl, and NH—R₅, wherein R₅ is a substituent selected from the group consisting of hydrogen, hydroxy, an alkoxy, sulfhydryl, nitro, amino, a halo, an aryloxy, cyano, an alkyl, a cycloalkyl, a heterocycloalkyl, an alkenyl, an alkynyl, an aryl, a heteroaryl, an arylalkyl and a heteroarylalkyl, wherein said substituent is unsubstituted or substituted.

5. The method of claim 4, wherein said heteroatoms are selected from the group consisting of oxygen, nitrogen and sulfur.

6. The method of claim 4, wherein said substituent is substituted with one to three groups, which can be the same or different and are selected from the group consisting of an alkyl, an alkenyl, an alkynyl, =O, a halo, hydroxy, a lower alkoxy, carboxy, a carboalkoxy, a carboxamido, cyano, carbonyl, —NO₂, an alkylthio, sulfoxide, sulfone, acylamino, amidino, an aryl, a heteroaryl, an aryloxy, and a heteroaryloxy.

7. The method of claim 1, wherein said NAT is NAT-1 and said inhibitor is selected from the group consisting of para-amino-salicylate (PAS) and para-amino-benzoic acid (PABA).

8. The method of claim 1, wherein said NAT is NAT-2 and said inhibitor is selected from the group consisting of dichlorphenamide, sulphamethazine (SMZ), dapsone (DDS) and isoniazid (INH).

9. The method of claim 2, wherein acetylation of said substrate predisposes the mammal to a disease.

10. The method of claim 9, wherein said inhibitor is administered prophylactically to inhibit acetylation of said substrate.

11. The method of claim 4, wherein NAT is in a mammal and acetylation of said substrate predisposes the mammal to a disease.

12. The method of claim 11, wherein said inhibitor is administered prophylactically to inhibit acetylation of said substrate.

13. The method of claim 1, wherein said substrate is a drug.

14. The method of claim 13, wherein said drug is an anticancer drug, an aminosalicylate, sulfasalazine, or a sulfonamide.

15. The method of claim 13, wherein acetylation of said drug adversely affects its therapeutic or prophylactic effect.

16. The method of claim 4, wherein said substrate is a drug.

17. The method of claim 16, wherein said drug is an anticancer drug, an aminosalicylate, sulfasalazine, or a sulfonamide.

18. The method of claim 16 wherein acetylation of said drug adversely affects its therapeutic or prophylactic effect.

19. The method of claim 1, wherein said substrate and said inhibitor are co-administered.

20. The method of claim 13, wherein said substrate and said inhibitor are co-administered.

21. The method of claim 16, wherein said substrate and said inhibitor are co-administered.

22. A pharmaceutical composition comprising:
(i) a compound comprising an arylamine group,
(ii) an inhibitor, wherein said inhibitor interacts with NAT to inhibit NAT from acetylating said arylamine group in said compound and wherein said inhibitor is present in said composition in an amount sufficient to inhibit acetylation of the arylamine group in the compound, and
(iii) a pharmaceutically acceptable carrier.

23. The composition of claim 22, wherein said inhibitor comprises an arylamine group that can be acetylated by NAT.

24. The composition of claim 22, wherein said inhibitor is a compound of formula:

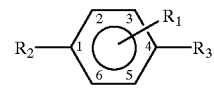

wherein one or more carbon atoms at positions 2, 3, 5 or 6 can be heteroatoms, which can be the same or different, wherein R₁ is one or more substituents, which can be the same or different, selected from the group consisting of hydrogen, hydroxy, an alkoxy, sulfhydryl, nitro, amino, a halo, an aryloxy, cyano, —[SO₂—R4], an alkyl, a cycloalkyl, a heterocycloalkyl, an alkenyl, an alkynyl, an aryl, a heteroaryl, an arylalkyl and a heteroarylalkyl, wherein R₂ is a substituent selected from the group consisting of amino, carboxyamide, sulfamide, —[NH—NH₂], —[SO₂—NH—NH₂] and —[CO—NH—NH₂], wherein R₃ is a substituent selected from the group consisting of hydrogen, hydroxy, an alkoxy, sulfhydryl, nitro, amino, a halo, an aryloxy, cyano, —[SO₂—R₄], an alkyl, a cycloalkyl, a heterocycloalkyl, an alkenyl, an alkynyl, an aryl, a heteroaryl, an arylalkyl and a heteroarylalkyl, wherein R₄ is a substituent selected from the group consisting of hydrogen, hydroxy, an alkoxy, sulfhydryl, nitro, amino, a halo, an aryloxy, cyano, an alkyl, a cycloalkyl, a heterocycloalkyl, an alkenyl, an alkynyl, an aryl, a heteroaryl, an arylalkyl, a heteroarylalkyl, and NH—R₅, wherein R₅ is a substituent selected from the group consisting of hydrogen, hydroxy, an alkoxy, sulfhydryl, nitro, amino, a halo, an aryloxy, cyano, an alkyl, a cycloalkyl, a heterocycloalkyl, an alkenyl, an alkynyl, an aryl, a heteroaryl, an arylalkyl and a heteroarylalkyl, wherein said substituent is unsubstituted or substituted.

25. The composition of claim 24, wherein said heteroatoms are selected from the group consisting of oxygen, nitrogen and sulfur.

26. The composition of claim 24, wherein said substituent is substituted with one to three groups, which can be the same or different and are selected from the group consisting of an alkyl, an alkenyl, an alkynyl, =O, a halo, hydroxy, a lower alkoxy, carboxy, a carboalkoxy, a carboxamido, cyano, carbonyl, —NO$_2$, an alkylthio, sulfoxide, sulfone, acylamino, amidino, an aryl, a heteroaryl, an aryloxy and a heteroaryloxy.

27. The composition of claim 22, wherein said inhibitor is PAS, PABA, dichlorphenamide, SMZ, DDS or INH.

28. The composition of claim 22, wherein said compound is an aminosalicylate, sulfasalazine, a sulfonamide or an anticancer drug.

29. The composition of claim 28, wherein said anticancer drug is aminoglutethimide, amonafide or batracylin.

30. The composition of claim 24, wherein said compound is an aminosalicylate, sulfasalazine, a sulfonamide or an anticancer drug.

31. The composition of claim 30, wherein said anticancer drug is aminoglutethimide, amonafide or batracylin.

32. The method of claim 2, wherein the mammal is a human.

33. The method of claim 2, wherein said substrate is a procarcinogen.

34. The method of claim 4, wherein NAT is in a mammal and wherein said substrate is a procarcinogen.

35. The method of claim 2, wherein acetylation of said substrate results in the formation of a carcinogenic product.

36. The method of claim 4, wherein acetylation of said substrate results in the formation of a carcinogenic product.

* * * * *